United States Patent [19]

Swerdlow et al.

[11] Patent Number: 5,935,522
[45] Date of Patent: *Aug. 10, 1999

[54] ON-LINE DNA ANALYSIS SYSTEM WITH RAPID THERMAL CYCLING

[75] Inventors: Harold P. Swerdlow; Carl T. Wittwer, both of Salt Lake City, Utah

[73] Assignee: University of Utah Research Foundation, Salt Lake City, Utah

[ * ] Notice: This patent issued on a continued prosecution application filed under 37 CFR 1.53(d), and is subject to the twenty year patent term provisions of 35 U.S.C. 154(a)(2).

[21] Appl. No.: 08/885,625

[22] Filed: Jun. 30, 1997

Related U.S. Application Data

[63] Continuation of application No. 08/885,625, Jun. 30, 1997, which is a continuation of application No. 08/381,703, Jan. 31, 1995, abandoned, which is a continuation-in-part of application No. 08/179,969, Jan. 10, 1994, Pat. No. 5,455,175, which is a continuation-in-part of application No. 07/815,966, Jan. 2, 1992, abandoned, which is a continuation-in-part of application No. 07/534,029, Jun. 4, 1990, abandoned.

[51] Int. Cl.$^6$ .................................................... G01N 35/10
[52] U.S. Cl. .......................... 422/70; 422/68.1; 422/81; 422/82.08; 436/43; 436/53; 436/161; 436/172; 436/174; 436/177; 436/178; 436/807; 204/601; 204/604; 210/142; 210/198.2; 210/656; 435/286.1; 435/287.2; 435/4; 435/6; 73/61.55; 73/61.56
[58] Field of Search ................................. 422/67, 70, 81, 422/82.05, 82.08, 100, 101, 68.1; 436/43, 53, 164, 165, 174, 177, 178, 180, 161, 162, 807; 204/180.1, 299 R, 601, 604; 210/198.2, 656, 142; 73/61.52, 61.55, 61.56; 435/4, 6, 286.1, 287.2

[56] References Cited

U.S. PATENT DOCUMENTS 1,006,767  10/1911  Mauger .
1,456,005  5/1923  Harris .
2,379,474  7/1945  Bramson .

(List continued on next page.)

FOREIGN PATENT DOCUMENTS 528 259  of 0000  Australia .
0 229 943 A2  1/1985  European Pat. Off. .

(List continued on next page.)

OTHER PUBLICATIONS

Barinaga, M., "Biotech Nightmare: Does Cetus Own PCR?," *Science,* vol. 251, pp. 739–740 (Feb. 1991).

(List continued on next page.)

*Primary Examiner*—Long V. Le
*Attorney, Agent, or Firm*—Thorpe, North & Western, L.L.P.

[57] ABSTRACT

An apparatus particularly suited for subjecting biological samples to any necessary sample preparation tasks, subjecting the sample to rapid thermal cycling, and then subjecting the sample to subsequent on-line analysis using one or more of a number of analytical techniques. The apparatus includes a chromatography device including an injection means, a chromatography pump, and a chromatography column. In addition, the apparatus also contains a capillary electrophoresis device consisting of a capillary electrophoresis column with an inlet and outlet end, a means of injection, and means of applying a high voltage to cause the differential migration of species of interest through the capillary column. Effluent from the liquid chromatography column passes over the inlet end of the capillary electrophoresis column through a tee structure and when the loading of the capillary electrophoresis column is desired, a voltage supply is activated at a precise voltage and polarity over a specific duration to cause sample species to be diverted from the flowing stream to the capillary electrophoresis column. A laser induced fluorescence detector preferably is used to analyze the products separated while in the electrophoresis column.

13 Claims, 5 Drawing Sheets

U.S. PATENT DOCUMENTS

| | | |
|---|---|---|
| 3,219,416 | 11/1965 | Natelson . |
| 3,556,659 | 1/1971 | Hawes . |
| 3,616,264 | 10/1971 | Ray et al. . |
| 3,999,868 | 12/1976 | Sanz et al. . |
| 4,038,055 | 7/1977 | Varano et al. . |
| 4,168,017 | 9/1979 | Anderwald . |
| 4,286,456 | 9/1981 | Sisti et al. . |
| 4,420,679 | 12/1983 | Howe . |
| 4,468,423 | 8/1984 | Hall . |
| 4,481,405 | 11/1984 | Malick . |
| 4,599,169 | 7/1986 | Ray ......................................... 210/175 |
| 4,675,300 | 6/1987 | Zare et al. . |
| 4,683,195 | 7/1987 | Mullis et al. . |
| 4,683,202 | 7/1987 | Mullis . |
| 4,684,465 | 8/1987 | Leaseburge et al. ................. 210/198.2 |
| 4,701,415 | 10/1987 | Dutton et al. . |
| 4,708,782 | 11/1987 | Andresen et al. ................... 204/299 R |
| 4,729,947 | 3/1988 | Middendorf et al. ....................... 435/6 |
| 4,826,319 | 5/1989 | Namba et al. . |
| 4,865,986 | 9/1989 | Coy et al. . |
| 4,868,103 | 9/1989 | Stavrianopoulos et al. . |
| 4,889,818 | 12/1989 | Gelfand et al. . |
| 4,902,624 | 2/1990 | Columbus et al. . |
| 4,908,112 | 3/1990 | Pace . |
| 4,965,188 | 10/1990 | Mullis et al. . |
| 4,981,801 | 1/1991 | Suzuki et al. . |
| 5,038,852 | 8/1991 | Johnson et al. . |
| 5,114,551 | 5/1992 | Hjerten et al. ......................... 204/180.1 |
| 5,116,471 | 5/1992 | Chien et al. . |
| 5,131,998 | 7/1992 | Jorgenson et al. . |
| 5,137,695 | 8/1992 | Rusnak et al. . |
| 5,141,621 | 8/1992 | Zare et al. . |
| 5,169,521 | 12/1992 | Oka et al. ............................ 210/198.2 |
| 5,173,163 | 12/1992 | Tehrani . |
| 5,174,962 | 12/1992 | Brennan ................................... 422/78 |
| 5,187,084 | 2/1993 | Hallsby . |
| 5,234,586 | 8/1993 | Afeyan et al. ......................... 210/198.2 |
| 5,235,586 | 8/1993 | Afeyan et al. . |
| 5,240,577 | 8/1993 | Jorgenson et al. . |
| 5,268,486 | 12/1993 | Waggoner et al. . |
| 5,316,913 | 5/1994 | Butcher et al. . |
| 5,333,675 | 8/1994 | Mullis et al. . |
| 5,346,672 | 9/1994 | Stapleton et al. . |
| 5,348,853 | 9/1994 | Wang et al. . |
| 5,364,790 | 11/1994 | Atwood et al. . |
| 5,380,489 | 1/1995 | Sutton et al. . |
| 5,415,839 | 5/1995 | Zaun et al. . |
| 5,425,921 | 6/1995 | Coakley et al. . |
| 5,436,134 | 7/1995 | Haugland et al. . |
| 5,449,621 | 9/1995 | Klein . |
| 5,455,175 | 10/1995 | Wittwer et al. . |
| 5,563,037 | 10/1996 | Sutherland et al. . |
| 5,565,322 | 10/1996 | Heller . |
| 5,599,504 | 2/1997 | Hosoi et al. . |
| 5,639,423 | 6/1997 | Northrup et al. ......................... 122/50 |
| 5,858,242 | 1/1999 | Bouma et al. . |

FOREIGN PATENT DOCUMENTS

| | | |
|---|---|---|
| 0 171 140A2 | 5/1985 | European Pat. Off. . |
| 0 211 334 A1 | 7/1986 | European Pat. Off. . |
| 0 236 069 A2 | 2/1987 | European Pat. Off. . |
| 0 488 769 A2 | 1/1991 | European Pat. Off. . |
| 0 459 241 A1 | 5/1991 | European Pat. Off. . |
| 0 475 760 A2 | 9/1991 | European Pat. Off. . |
| 0 566 751 A1 | 3/1992 | European Pat. Off. . |
| 0 519 623 A2 | 6/1992 | European Pat. Off. . |
| 0 580 362 A1 | 7/1993 | European Pat. Off. . |
| 0 636 413 A2 | 7/1994 | European Pat. Off. . |
| 0 640 828 A1 | 8/1994 | European Pat. Off. . |
| 0 711 840 A2 | 11/1995 | European Pat. Off. . |
| 0 805 190 A2 | 5/1997 | European Pat. Off. . |
| 3 808 942 A1 | 9/1989 | Germany . |
| 6 212 986 | 3/1987 | Japan . |
| 7-31500 | 3/1995 | Japan . |
| WO 89 09437 | 10/1989 | WIPO . |
| WO 92 20778 | 11/1992 | WIPO . |
| WO 93 16194 | 8/1993 | WIPO . |
| WO 93 20240 | 10/1993 | WIPO . |
| WO 94 27137 | 11/1994 | WIPO . |
| WO 95 21266 | 1/1995 | WIPO . |
| WO 95 21382 | 8/1995 | WIPO . |
| WO 95 21938 | 8/1995 | WIPO . |
| WO 95 30139 | 11/1995 | WIPO . |
| WO 95 32306 | 11/1995 | WIPO . |
| 97 09620 | 6/1997 | WIPO . |
| 97 09856 | 6/1997 | WIPO . |

OTHER PUBLICATIONS

Barinaga, M., "And the Winner: Cetus Does Own PCR," *Science,* vol. 251, p. 1174 (Feb. 1991).

Barinaga, M., "A Personal Technology Transfer Effort in DNA Diagnostics: Biochemist Eva Harris Introduces DNA Techniques to Nicaragua," *Science,* vol. 266, No. 5189, p. 1317 (Nov. 25, 1994).

Barnes, W.M., "PCR Amplification of up to 35–kb DNA with High Fidelity and High Yield from λ Bacteriophage Templates," *Proc. Natl. Acad. Sci. USA,* vol. 91, pp. 2216–2220 (1994).

Bertina, R., et al., "Mutation in Blood Coagulation Factor v. Associated with resistance to actuated proteen," *Letters to Nature,* vol. 369, pp. 64–67 (May 1994).

Brow, M.D., "The Polymerase Chain Reaction," (Book Reviews Section) *Science,* vol. 265, No. 5173, p. 817 (Aug. 5, 1994).

Brown, A.B., et al., "Raid Cycle Amplification For Construction of Competitive Templates," *Genetic Engineering with PCR,* Edited by: Horton, R.M., Horizon Scientific Press, Wymondham, U.K., Chap. 4 (1997).

Cao, T.M., "A Simple and Inexpensive System to Amplify DNA by PCR," *BioTechniques,* vol. 7, No. 6, pp. 566–567 (1989).

Cardullo, R.A., et al., "Detection of Nucleic Acid Hybridization by Nonradiative Fluorescence Resonance Energy Transfer," *Proc. Natl. Acad. Sci. USA,* vol. 85, pp. 8790–8794 (1988).

Chase, M., "Cetus is Victor in Patent fight with DuPont," *Wall Street Journal,* Feb. 28, 1991.

Convey, E., "Futuristic Studies: South Shore Hospital Tests DNA," *Boston Business Journal,* vol. 15, No. 11, Sec. 1, p. 9, Apr. 28, 1995.

Denton, P., et al., "A Low–Cost Air Driven Cycling Oven," *PCR Protocals: A Guide to Methods and Applications,* Edited by M.A. Innis, et al., Academic Press, Inc., San Diego, Chap. 52, pp. 535–541 (1990).

Findlay, J.B., et al., "Automated Closed–Vessel System for In Vitro Diagnostics Based on Polymerase CHain Reaction," *Clinical Chemistry,* vol. 39, No. 9, pp. 1927–1933 (1993).

Chosh, S.S., et al., "Real Time Kinetics of Reduction Endonuclease Cleavage Monitored by Fluorescence Resonance Energy Transfer," *Nucleic Acids Research,* vol. 22, No. 15, pp. 3155–3159 (1994).

Goldner, H., "PCR update: New Techniques Multiply Uses," *R& D Magazine,* vol. 36, Noi. 4, p. 55 (Mar. 1994).

Graham, A., "A Haystack of Needles: Applying the Polymerase Chain Reaction," *Chemistry and Industry,* No. 18, p. 718.

Gustafson, C.E., et al., "Effect of Heat Denaturation of Target DNA on the PCR Amplication," *Gene,* vol. 123, p. 241–244 (1993).

Higuchi, R., et al., "Simultaneous Amplifications and Detection of Specific DNA Sequences," *Bio/Technology,* vo. 10, pp. 413–417 (1992).

Higuchi, R., et al., "Kinetic PCR analysis: Real–time Monitoring of DNA Amplification Reactions," *Bio–Technology,* vol. 11, pp. 1026–1030 (1993).

Hillen, W., et al., High Resolution Experimental and Theoretical thermal Denaturation Studies on Small Overlapping Restriction Fragments Containing the *Escherichia coli* Lactose Genetic Control Region, *The Journal of Biological Chemistry,* vol. 256, No. 6, pp. 2761–2766 (1981).

Hiyoshi, M., et al., "Assay of DNA Denaturation by Polymerase Chain Reaction–Driven Fluorescence Resonance Energy Transfer," *Analytical Biochemistry,* vol. 221, pp. 306–311 (1994).

Hoffman, L.M., et al., "Use of a Gas Chromatograph Oven for DNA Amplification by the Polymerase Chain Reaction," *BioTechniques,* vol. 6, No. 10, pp. 932–936 (1988).

Holland, P.M., et al., Detection of Specific Polymerase Chain ReactionProduct by Utilizxing the 5'→3' Exonuclease Activity of *Thermas Aquaticus* DNA Polymerase, *Proc. Natl. Acad. Sci. USA,* vol. 88, pp. 7276–7280 (1991).

Hopfenbeck, J.A., et al., "Digozigenin–Labeled Probes Amplified from Genomic DNA Detect T–Cell Gene Rearrangements," *American Journal fo Clinical Pahtology,* vol. 97, No. 5, pp. 638–644 (1992).

Ishiguro, T., et al., "Homogeneous Quantitative Assay of Hepatitis C Virus RNA by Polymerase Chain Reaction in the Presence of a Flourescent Intercalater," *Analytical Biochemistry,* vol. 229, pp. 207–213 (1995).

Kang, J., et al., "Exact Quantification of DNA–RNA Copy Numbers by PCR–TGGE," *PCR Strategies,* Academic Press, Inc., Chap 15, pp. 189–198 (1995).

Ke, S., et al., "Influence of Nearest Neighbor Sequence on the Stability of Base pair Mismatches in Long DNA: Determined by Temperature–Gradient Gel Electrophoresis," *Nucleic Acids Research,* vol. 21, No. 22, pp. 5137–5143 (1993).

Lee, L.G., et al., "Allelic Discrimination by Nick–Translation PCR with Fluorgenic Probes," *Nucleic Acids Research,* vol. 21, No. 16, op. 3761–3766 (1993).

Linz, U., "Thermocycler Temperature Variation Invalidates PCR Results," *BioTechniques,* vol. 9, No. 3, pp. 386–392 (1990).

Livak, K.J., et al., "Oligonucleotides with Fluorescent Dyes at Opposite Ends Provide A Quenched Probe System Useful for Detecting PCR Product and Nucleic Acids Hybridization," *PCR Methods and Applications,* vol. 4, pp. 357–362 (1995).

Matthews, J., et al,. "Analytical Strategies for the Use of DNA Probes," *Review,* Feb. 25, 1988.

Morrison, L.E., Detection of Energy Transfer and Fluorescence Quenching, *Nonisotopic DNA Probe Techniques,* Edited by: Larry J. Kricka, Academic Press, Inc., San Diego, Chap. 13, pp. 311–352 (1992).

Morrison, L.E., et al., "Sensitive Fluorescence–Based Thermodynamic and Kinetic Measurements of DNA Hybridization in Solution," *Biochemistry,* vol. 32, pp. 3905–3104 (1993).

Mujumdar, Ratnakar B., et al., "Cynanine Dye Labeling Reagents Contsining Isothiocyanate Groups," *Cytometry,* vol. 10, pp. 11–19 (1989).

Nilsson, P., et al., "Real–Time Monitoring of DNA Manipulations Using Biosensor Technology," *Analytical Biochemistry,* vol. 224, pp. 400–408 (1995).

Oste, C.C., "PCR Instrumentation: Where Do We Stand?," *The Polymerase Chain Reaction,* Edited by Mullis, et al., Birkhauser, Boston, Chap. 14 (1994).

Perry, R.H., et al., Heat Transmission by Radiation, *Chemical Engineers' Handbook,* 5th ed., McGraw Hill Book Co., New York, Chap. 10, pp. 48–56 (????).

Ririe, K.M., et al., "Product Differentiation by Analysios of DNA Melting Curves during the Polymerase Chain Reaction," *Analytical Biochemistry,* vol. 24, pp. 154–160 (1997).

Segal, G.H., et al., "Identification of Monoclonal B–Cell Population by Rapid Cycle Polymerase Chain Reaction," *The American Journal of Pathology,* vol. 141, No. 6, pp. 1291–1297 (1992).

Service, R.E., "The Incredible Shrinking Laboratory: Microchips Allow Miniturization of Analytical Laboatories," *Science,* vol. 268, No. 5207, p. 26 (Apr. 1995).

Stimpson, D.I., "Real–Time Detectionof DNA Hybridization and Melting on Oligonucleotide Arrays by Using Optical Wave Guides," *Proc. Natl. Acad. Sci. USA,* vol. 92, pp. 6379–6383 (1995).

Swerdlow, H., et al., "Fully Automated DNA Reaction and Analysis in a Fluidic Capillary Instrument," *Anal. Chem.,* vol. 69, pp. 848–855 (1997).

Swerdlow, H., "Background and Significance . . . ," *PHS 398* (Rev. Sep. 1991), pp. 27–55.

Tombler, E.R., et al., "Spectrofluorometric Assay for Hybridization of Oligodeozynucleotides Using Ethidium Dimer," *BioTechniques,* vol. 15, No. 6, pp. 1060–1064 (1993).

Tyagi, S., et al,. "Molecular Beacons: Probes that Fluoresce Upon Hybridization," *Nature Biotechnology,* vol. 14, pp. 301–308 (1996).

Voorberg, J., et al., "Association of Idiopathic venous thromboembulism with single pointmuatation at Arg of Factor V," *Short Reports,* vol. 343 (Jun. 18, 1994).

Weis, J.H., et al., "Detection of Rare mRNAs via Quantitative RT–PCR," *Trends in Genetics,* vol. 8, No. 8, pp. 263–264 (1992).

Wilding, et al., "PCR in Silicon Microstructure," *Clinical Chemistry,* vol. 40, No. 9, pp. 1815–1818 (1994).

Willard, H.H., et al., "Gas Chromatography," *Instrumental in Methods of Analysis,* 6th ed., Wadsworth Publishing CO., Belmont, CA, Chap. 16, p. 454 (????).

Wittwer, C.T., et al., "Minimizing the Time Required for DNA Amplification by Efficient Heat Transfer to Small Samples," *Analytical Biochemsitry,* vol. 186, pp. 328–331 (1990).

Wittwer, C.T., et al,. "Automated Polymerase Chain Reaction in Capillary Tubes with Hot Air," *Nucleic Acids Research,* vol.17, No. 11, pp. 4353–4357 (1989).

Wittwer, C.T., et al,. "Rapid Cycle DNA Amplification: Time nad Temperature Optimization," *BioTechniques,* vol. 10, No. 1, pp. 76–83 (1991).

Wittwer, C.T., et al,. "Rapid Cycle Allel–Specific Amplification: Studies with the Cystic Fibrosis $\Delta F_{508}$Locus." *Clinical Chemistry,* vol. 39, No. 5, pp. 804–809 (1993).

Wittwer, C.T., et al., "Rapid Cycle DNA Amplification," *The Polymerase Chain Reaction,* Edited by: Mullis, et al., Birkhauser, Boston, Chap. 15 (1994).

Wittwer, C.T., et al., "Continuous Fluorescence Monitoring of Rapid Cycle DNA Amplification," *BioTechniques,* vol. 22, pp. 130–138 (1997).

Wittwer, C.T., et al., "The LightCycler: A Microvolume Multisample Fluorimeter with Rapid Temperature Control," *BioTechniques*, vol. 22, pp. 176–181 (1997).
Wittwer, C.T., et al., "Fluorscence Monitoring of Rapid Cycle PCR For Quantification," *Gene Quantification*, Edited by: Ferre, F., Birkhauser, Boston (1997).
Yguerabide, J., et al., "Quantitative Fluorescence Method for Continuous Measurement of DNA Hybridization Kinetics Using a Fluorescenct Intercalator," *Analytical Biochemistry*, vol. 228, pp. 208–220 (1995).
Biotherm Corporation Advertisement, BioOven (1991).
Ericorp Advertisement, Twinblock System (1991).
Techne Advertisement, PHC–1 Dri–Block (1988).
Hybaid Advertisement, Hybaid Heating and Cooling Block (1988).
Eppendorf Advertisement, Eppendorf MicroCylcer (1988).
COY Advertisement, Tempcycler Model 50 Microtube Incubator (1991).
Idaho Technology Advertisement and Specification Sheets for 1605 Product (1991).
Perkin–Elmer Advertisement, ABI Prism 7700 Sequence Detection system (1991).
Clark, et al,. "Cassettes Simplify SMall–Sample Dialysis," R & D Magazine, p. 31, Sep. 1995.
"Let the Microchip Fall Where Diagnostics Lies: Implications: Affymetrix: DNA on a Chip," Genesis Report–Dx, vol. 4, No. 3 (1994).
"PCR Detection Blows Cover on Lyme disease, Q Fever," Biotechnology Newswatch, vol. 10, No. 1 (Jan. 1990).
"Perkin–Elmer and Fisher Scientific announce distribution Agreement; Fisher to Sell Perkin–Elmer's GENEAMP(R) PCR System 2400," Business Wire, Mar. 30, 1995.
Fisher 88, Fisher Scientific Catalogue, Instrumentation Laboratory.
Operation Manual for HP–5880A Gas Chromatograph.
Operation Manual for the MIC 6000.

ON-LINE DNA ANALYSIS SYSTEM WITH RAPID THERMAL CYCLING

This application is a continuation of U.S. patent application Ser. No. 08/885,625 filed Jun. 30, 1997 entitled On-line DNA Analysis System with Rapid Thermal Cycling which is a continuation of U.S. patent application Ser. No. 08/381,703 filed Jan. 31, 1995 entitled On-line DNA Analysis System with Rapid Thermal Cycling, now abandoned, which is a continuation-in-part of U.S. patent application Ser. No. 08/179,969 filed Jan. 10, 1994, now U.S. Pat. No. 5,455,175, entitled Rapid Thermal Cycling Device which is a continuation-in-part of U.S. patent application Ser. No. 07/815,966 filed Jan. 2, 1992 entitled Rapid Thermal Cycling Device, now abandoned, which is a continuation-in-part of U.S. patent application Ser. No. 07/534,029 filed Jun. 4, 1990, entitled Automated Polymerase Chain Reaction Device, now abandoned, all of which are incorporated herein by reference in their entireties.

This invention was made with Government support under Contract No. DE-AC05-76OR00033 awarded by the Department of Energy and Contract No. 5P30HG00199 awarded by the National Institutes of Health. The Government has certain rights in this invention.

BACKGROUND

1. The Field of the Invention

The invention relates generally to apparatus for analysis of biological samples which are subjected to rapid change of temperature. More specifically, the present invention relates to the direct, on-line analysis of DNA products derived from a thermal cycling apparatus.

2. The Background Art

The recent efforts to discover the genetic basis for human beings has raised the promise of cures for diseases heretofore incurable, the promise of extending the life of humans, and the promise of generally improving the quality of life for humans. The Human Genome Project being spearheaded in the United States is a major step toward realizing these promises which genetic engineering and its related technological areas have in store. Disadvantageously, discovering the entire DNA sequence of any mammal is a mammoth undertaking and the available technology is far behind the rate which is necessary if the Human Genome Project is to be completed in a reasonable period of time.

While alternative technologies have been proposed to simplify or speed up DNA sequencing, techniques using dideoxy reactions and gel electrophoresis still remain at the core of most efforts to improve DNA sequencing technology. Recent advances in gel-based methods have brought DNA sequencing technology to the rate of sequencing about one megabase per year but not to the megabase per day rates needed to complete the Human Genome Project in a reasonable period of time.

Even though techniques such as ultra-thin slab gel electrophoresis have improved to the point of carrying out electrophoresis separations at a desirable rate, (See Stegemann, J., Schwager, C., Erfle, H., Hewitt, N., Voss, H. Zimmerman, J. and Ansorge, W. (1991), Highspeed on-line DNA sequencing on ultrathin slab gels, *Nucleic Acids Res.* 19, 675–676; Kostichka, A. J., Marchbanks, M. L., Brumley, R. L., Jr., Drossman, H. and Smith, L. M. (1992), High speed automated DNA sequencing in ultrathin slab gels, *Bio/Technology* 10, 78–81) and multiple capillary electrophoresis devices have been built (Taylor, J. A. and Yeung, E. A. (1993), Multiplexed fluorescence detector for capillary electrophoresis using axial optical fiber illumination, *Anal. Chem.* 65, 956–960; Ueno, K. and Yeung, E. S. (1994), Simultaneous monitoring of DNA fragments separated by electrophoresis in a multiplexed array of 100 capillaries, *Anal. Chem.* 66, 1424–1431; Kambara, H. and Takahashi, S. (1993) Multiple-sheathflow capillary array DNA analyzer, *Nature* 361, 565–566; Takahashi, S., Murakami, K., Anazawa, T. and Kambara, H. (1994) Multiple sheath-flow gel capillary-array electrophoresis for multicolor fluorescent DNA detection, *Anal. Chem.* 66, 1021–1026; Huang, X. C., Quesada, M. A. and Mathies, R. A. (1992), Capillary array electrophoresis using laser-excited confocal fluorescence detection, *Anal. Chem.* 64, 967–972; Clark, S. M. and Mathies, R. A. (1993) High-speed parallel separation of DNA restriction fragments using capillary array electrophoresis, *Anal. Biochem.* 215, 163–170), the problem which has not been recognized in the art, or at least not solved, is that of feeding such electrophoresis instruments at the voracious rate at which they are capable of carrying out their procedures. It has not been recognized in the art that the front-end tasks of preparing samples for processing by these electrophoresis techniques have recently become the rate-limiting step in DNA analysis and particularly in DNA sequencing. Such front-end tasks include generation of libraries, ordering the large fragments and mapping and subcloning of smaller fragments. Other important front-end tasks also involve the preparation of templates, performance of reactions, purification of reaction products and loading of samples, before electrophoresis can begin.

It would be a significant advance in the art to provide a system which can carry out such front-end tasks quickly, efficiently, and accurately.

In particular, the front-end task of reliably and reproducibly subjecting relatively small DNA samples to thermal cycling has generally been an extremely time consuming step. Cyclic DNA amplification, using a thermostable DNA polymerase, allows automated amplification of specific DNA, widely known as the polymerase chain reaction or PCR. Automation of this process requires controlled and precise thermal cycling of reaction mixtures usually contained in a plurality of containers. In the past, the container of preference has been a standard, plastic microfuge tube.

Commercial programmable metal heat blocks have been used in the past to carry out the temperature cycling of samples in microfuge tubes through the desired temperature versus time profile. However, the inability to quickly and accurately adjust the temperature of the heater block through a large temperature range over a short time period, has rendered the use of the heater block type devices undesirable as a heat control system when carrying out the polymerase chain reaction.

Moreover, the microfuge tubes which are generally used have disadvantages. The material of the microfuge tubes, their wall thickness, and the geometry of the microfuge tubes is a hindrance to rapid heating and cooling of the sample contained therein. The plastic material and the thickness of the wall of microfuge tubes act as an insulator between the sample contained therein and the surrounding medium thus hindering transfer of thermal energy. Also, the geometry of the microfuge tube presents a small surface area to whatever medium is being used to transfer thermal energy. The continued use of microfuge tubes in the art, with their suboptimal geometry, indicates that the benefits of improved thermal transfer (which come by increasing the surface area of the sample container for samples of constant volume) has not been generally recognized in the art.

Furthermore, devices using water baths with fluidic switching (or mechanical transfer) have also been used as a thermal cycler for the polymerase chain reaction. Although water baths have been used in cycling a PCR mixture through a desired temperature versus time profile necessary for the reaction to take place, the high thermal mass of the water (and the low thermal conductivity of plastic microfuge tubes) has been significantly limiting as far as performance of the apparatus and the yields of the reaction are concerned.

Devices using water baths provide very slow thermal cycling performance and the yields of the reaction are less than desirable. This is because the water's thermal mass significantly restricts the maximum temperature versus time gradient which can be achieved thereby. Also, the water bath apparatus has been found to be very cumbersome due to the size and number of water carrying hoses and external temperature controlling devices for the water. Further, the need for excessive periodic maintenance and inspection of the water fittings for the purpose of detecting leaks in a water bath apparatus is tedious and time consuming. Finally, it is difficult with the water bath apparatus to control the temperature in the sample tubes with the desired accuracy.

U.S. Pat. No. 3,616,264 to Ray shows a thermal forced air apparatus for cycling air to heat or cool biological samples to a constant temperature. Although the Ray device is somewhat effective in maintaining a constant temperature within an air chamber, it does not address the need for rapidly adjusting the temperature in a cyclical manner according to a temperature versus time profile such as the polymerase chain reaction.

U.S. Pat. No. 4,420,679 to Howe and U.S. Pat. No. 4,286,456 to Sisti et al. both disclose gas chromatographic ovens. The devices disclosed in the Howe and Sisti et al. patents are suited for carrying out gas chromatography procedures but do not provide thermal cycling which is substantially any more rapid than that provided by any of the earlier described devices. Rapid thermal cycling, while potentially useful for many procedures, is particularly advantageous for carrying out the PCR. Devices such as those described in the Howe and Sisti et al. patents are not suitable for efficiently and rapidly carrying out such reactions.

Sample contamination also remains a significant problem for the user as well. When performing DNA amplification, minute contamination of DNA from another source can have disastrous consequences to the final results and conclusions of the procedure. One source of sample contamination comes from the process of the amplification of DNA of other samples to be run. Sample transfer techniques using pipettors or other means can contaminate the process. Likewise, even careful technicians can transfer DNA directly from the technician's body to the samples thereby reducing the confidence in the overall PCR process. As a consequence, sample preparation for DNA analysis is frequently carried out in "clean rooms" or at other clean locations within the facility which significantly increases the cost and space requirements for performing quality PCR.

It would also be a great advance in the art to provide a fully contained and automated system which would protect the user from being exposed to the DNA which is being amplified, as well as to protect the samples from cross-contamination. Using available technology, the user must handle samples following thermal cycling which may contain significantly higher concentrations of hazardous DNA species in order to subject the samples to further analysis. Thus, the exposure of the user to the amplified DNA is a serious problem in the state of the art.

Another disadvantage of the current state of the art is that the time to first result is very long. The amplification of DNA is only one front-end step in a series of analytical steps needed to arrive at the desired result. The current procedures can require eight hours or more of amplification and analysis before the result is known. This severely limits the use of the PCR technology for many application areas where answers are desired in minutes. DNA amplification with on-line analysis would be advantageous to the user. The labor intensive procedures required in the currently available devices are a hinderance to the efficient use of PCR technology.

U.S. Pat. Nos. 5,240,577 and 5,131,998 (Jorgenson) teach that enhanced 2-dimensional resolution can be obtained by the combination of liquid chromatography and capillary electrophoresis. However, the Jorgenson references do not suggest or teach that other steps necessary to DNA analysis, for example PCR reaction, should be combined in an automated on-line system.

In view of the forgoing, it would be an advance in the art to provide a system which can automate and expedite DNA analysis, including DNA sequencing, and particularly which can carry out front-end tasks such as cyclical DNA amplification and which does not require labor-intensive intervention by a technician.

BRIEF SUMMARY AND OBJECTS OF THE INVENTION

In view of the above described state of the art, the present invention seeks to realize the following objects and advantages.

It is a primary object of the present invention to provide a DNA analysis system and method which requires minimal technician intervention.

It is also an object of the present invention to provide a DNA analysis system and method which reduces contamination of the procedure.

It is also an object of the present invention to provide a DNA sequencing system and method which can carry out sequencing much faster than previously possible.

It is another object of the present invention to provide a DNA analysis system which eliminates exposure of a technician to amplified DNA.

It is still another object of the present invention to provide a DNA analysis system which provides results faster than previously possible.

It is a further object of the present invention to provide a DNA analysis system which includes a rapid thermal cycling device coupled to a primary separation means and which automatically transfers said samples to the primary separation means at the proper time in the thermal cycle.

It is also an object of the present invention to provide a DNA analysis system which couples a primary separation means to a secondary separation means for further isolation of the species of interest.

It is also a further object of the present invention to provide a detection means in a DNA analysis system which can be utilized in conjunction with either or both a primary and a secondary separation means.

These and other objects and advantages of the invention will become more fully apparent from the description and claims which follow, or may be learned by the practice of the invention.

The present invention is an apparatus particularly suited for subjecting biological samples to any necessary sample preparation tasks, subjecting the sample to rapid thermal cycling, and then subjecting the sample to subsequent on-line analysis using one or more of a number of analytical techniques. In one of its preferred forms, the system includes a thermal cycling device in which a chamber for holding the sample is provided by a thermally insulated chamber designed to retain heat, and also a means for providing sufficient energy to heat the chamber at a rate at least as great as one degree centigrade per second repeatedly through a predetermined temperature cycle such that the temperature repeatedly ramps from a first temperature to at least a second higher temperature and ramps from at least the second temperature to a lower temperature in a rapid and controlled manner where said predetermined temperature cycle facilitates DNA amplification.

In order to rapidly cool the sample chamber, the preferred apparatus includes a means for forcing air into the sample chamber and a means for dispersing the air forced into the sample chamber. A high velocity fan functions to force air into the sample chamber and functions to disperse the air in the chamber. A means for venting allows the air to escape from the sample chamber taking the unwanted heat with it. The present invention allows heating and cooling of a sample to take place both quickly and uniformly.

The preferred sample container is a small diameter channel having an inner bore and an outer wall. The present embodiment utilizes a small bore tube and a valve to facilitate the introduction of the sample into the tubing located in the thermal chamber. The valve also functions to transfer the sample to a flowing stream and the primary separation means.

The preferred embodiment of the primary separation means is a chromatography apparatus including an injection means, a chromatography pump, and a column. Preferably, a micro column liquid chromatography technique is employed to reduce waste solvents and increase sample concentration in the flow channel at the outlet of the column.

Alternatively, the primary separation technique could be filter material, preferably a membrane filter designed to restrict the passage of large molecular weight samples thereby enriching the concentration of the large molecular weight component. In addition, the primary separation apparatus could also contain a capillary electrophoresis device consisting of a capillary electrophoresis column with an inlet and outlet end, means for injection, and means for applying a high voltage to cause the differential migration of species of interest through the capillary column.

In its preferred embodiments, the invention will utilize a capillary electrophoresis device as a secondary separation means including a capillary column with an inlet and an outlet end, an injection means, and a means of applying a suitable voltage to cause the separation to occur. In its current embodiment, the effluent from the primary separation step passes over the inlet end of the capillary electrophoresis column through a tee structure. When the loading of the capillary electrophoresis column is desired, a voltage supply is activated at a precise voltage and polarity over a specific duration to cause sample species to be diverted from the flowing stream to the capillary electrophoresis column.

Preferably, the capillary column has an optimum length and diameter and contains a buffer, viscous buffer, or a gel which assists the separation. Furthermore, the capillary and its media resists the flow of the excess fluid effluent from the primary separation step forcing it to be diverted to waste. Only ions of a specific charge will be injected into the capillary electrophoresis column due to the specific polarity of the applied voltage. Alternatively, the secondary separation technique could be one of a variety of separation techniques including, but not limited to liquid chromatography, field flow fractionation, or membrane filtration.

During electrophoresis, detection of the sample products is preferably accomplished by a laser-induced fluorescence detector which is mounted on the electrophoresis column. A number of other detection devices can also be used within the scope of the present invention. The results of the detection are preferably digitized and stored in a computing device. The computing device, accompanied by appropriate interface devices and software/firmware control, controls the operation of the system.

The present invention provides a system and method which is particularly suitable for rapid and accurate DNA analysis and particularly suitable for DNA sequencing.

BRIEF DESCRIPTION OF THE DRAWINGS

In order to better appreciate how the above-recited and other advantages and objects of the invention are obtained, a more particular description of the invention briefly described above will be rendered by reference to specific embodiments thereof which are illustrated in the appended drawings. Understanding that these drawings depict only typical embodiments of the invention and are not therefore to be considered limiting of its scope, the invention will be described and explained with additional specificity and detail through the use of the accompanying drawings in which.

DETAILED DESCRIPTION OF THE PREFERRED EMBODIMENTS

As will be appreciated shortly, the present invention provides an automated system which performs PCR reactions, preferably in a capillary tube, purifies the PCR product fragments, and loads the product fragments directly onto a separation capillary as well as performing other required steps. The present invention utilizes automated fluidic techniques which obviate the disadvantageous manual manipulations which must be carried out by a technician in the previously available devices. Furthermore, loading of samples is preferably performed on-line and the described embodiments provide a closed system which is easily sterilized in preparation for the next reaction. In particular, the present invention solves the problem of carrying out front-end DNA analysis tasks quickly and efficiently which has prevented DNA analysis, and particularly DNA sequencing, from achieving the rates which have been long desired in the art. Even those devices available in the art which automate one or two procedures and which utilize robotic techniques still do not achieve the beneficial results of the present invention.

Figure 1:
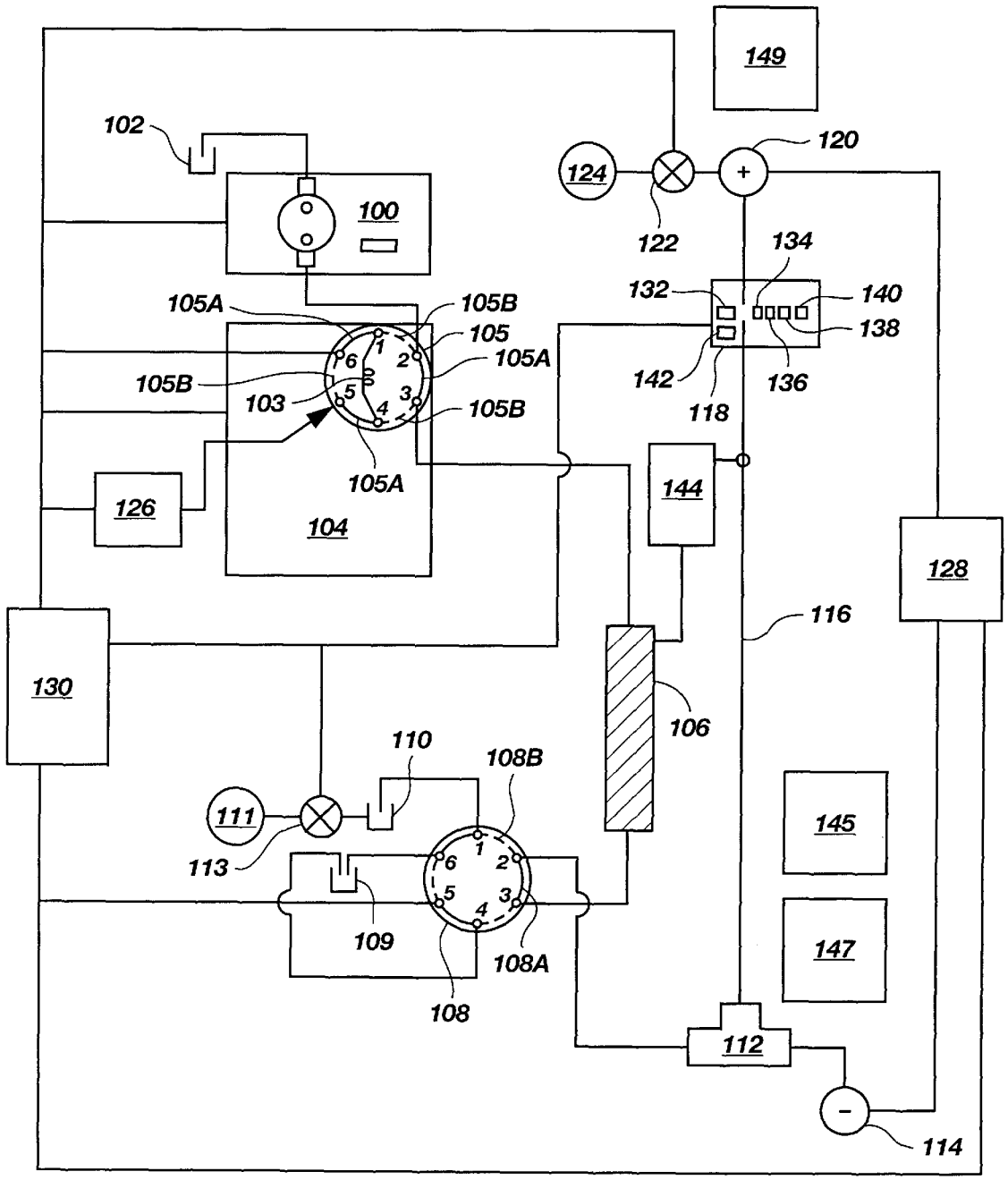
FIG. 1 is a schematic diagram of a first presently preferred embodiment of the present invention.

Reference will now be made to FIG. 1 which is a schematic diagram of a first presently preferred embodiment of the present invention. As will be appreciated shortly, in accordance with the present invention the embodiment of FIG. 1 provides the important feature of interfacing capillary PCR with capillary electrophoresis which provides advantages not heretofore recognized or available in the art.

A sample which is to undergo analysis is loaded onto a High Performance Liquid Chromatography (HPLC) system, which includes a pump 100, such as is known in the art. In order to provide the advantages of in-line fluidic transfer of the sample, an HPLC injection valve is mounted so its loop is projected into the sample chamber of a thermal cycling device 104.

As represented in FIG. 1, PCR is performed in the injection loop 103 of a High Performance Liquid Chromatography (HPLC) injection valve 105. The injection loop 103 of the injection valve 105 is located inside the thermal cycling device 104.

The thermal cycling device 104 is preferably a thermal cycler adapted to hold the samples in capillary tubes and air is used as the medium to rapidly transfer heat to and from the sample. A preferred thermal cycling device 104 is available from Idaho Technology as described in the publication: Swerdlow, H., Dew-Jager, K. E. and Gesteland, R. (1993) Rapid cycle sequencing in an air thermal cycler, BioTechniques 15, 512–519. The preferred thermal cycler is also described in U.S. patent application Ser. No. 08/179,969, filed Jan. 10, 1994 entitled Rapid Thermal Cycling Device which has been incorporated herein by reference.

The preferred thermal cycling device 104 is adapted to perform PCR reactions in small volume (for example 10 $\mu$l) in glass capillary tubes (having an exemplary inner diameter of 500 $\mu$m) more rapidly than otherwise possible using other techniques. Not only does the use of the preferred thermal cycling device 104 provide PCR reactions faster than otherwise available in the industry, the thermal cycler also provides a concomitant improvement in reaction specificity when compared to slower thermal cyclers using block structures or liquid bath techniques. Moreover, the preferred thermal cycling device 104 also provides improvements in cycle sequencing reactions performed in small volumes such as provided by capillary tubes.

The injection loop 103 is preferably fabricated from TEFLON™ tubing having about a 560 $\mu$m inner diameter and about a 860 $\mu$m outer diameter. The preferred inner diameter range for the tubing is about 100 $\mu$m to about 1000 $\mu$m and generally not greater than about 2500 $\mu$m so that the volume is kept small. The preferred tubing was chosen for the injection loop 103 to closely match the thermal characteristics of the glass capillary tubes which are ideally suited for use in the thermal cycling device 104.

The preferred injection loop 103 accommodates a sample volume of about 27 $\mu$l but it will be appreciated that the preferred range can vary greatly from this value. The small volume of sample and the thermal characteristics of the injection loop 103 allows the thermal cycling device 104 to carry out PCR very rapidly. With the injection valve 105 in the load position, represented by the solid line 105A, injection loop 103 is filled with sample. The injection valve 105 is rotated 30 degrees causing all ports in the injection valve 105 to be sealed and preventing thermal expansion or evaporative loss of the sample during thermal cycling imposed by the thermal cycling device 104. After the thermal cycling is complete, the injection valve 105 is returned to the load position 105A before moving to the injection position 105B and injecting the sample onto the HPLC column 106.

The above described preferred thermal cycling device available from Idaho Technologies and designated as the Air Thermo-Cycler is manufactured to receive 500 $\mu$m inner diameter, 1000 $\mu$m outer diameter, 10 cm glass capillary tubes which are heat sealed after being filled with sample to avoid evaporative losses and which performs very rapid PCR procedures. Those skilled in the art can readily adapt the described thermal cycling device to function in accordance with the present invention using the information contained herein.

One of the PCR primers which is utilized during the PCR procedure which takes place in the thermal cycler 104 is preferably labelled with a fluorescent dye which will be used by fluorescence detector 118 represented in FIG. 1. One such fluorescent dye which is preferred for use with the described embodiment and which is available in the industry can be obtained from Applied Biosystems (a division of Perkin-Elmer). A tetra-methyl rhodamine dye (TAMRA) which is part of Applied Biosystems' four color dye-primer sequencing system. Other well known fluorescent dye systems which can be used for DNA sequencing or PCR applications with embodiments of the present invention include DuPont's four color dye-terminators and deoxynucleotide triphosphates labeled with florescent moieties.

After being subjected to the thermal cycler 104, the sample is purified by a gel-filtration HPLC column 106 and is fed through a heart cut valve 108. The sample is then run through a tee device 112 past a capillary electrophoresis column 116. The tee 112 is preferably a molded or machined structure which allows the capillary electrophoresis column 116 to be inserted into, or adjacent to, the product flow stream flowing therethrough as will be explained more fully shortly. The capillary electrophoresis column 116 is preferably a polymer-filled capillary column into which the primer and product bands of the sample are loaded in a continuous fashion. During electrophoresis, detection of the sample products is accomplished by a laser-induced fluorescence detector 118 which is mounted on the capillary electrophoresis column 116. The capillary electrophoresis column 116 is refilled from a positive buffer chamber 120 in cooperation with the application of pressure from a pressure source 124, such as a pump, and a pneumatic valve system 122. The function of each of the principal components described above will be further explained below.

Referring still to FIG. 1, the apparatus components downstream of the thermal cycling device will now be explained further. As is known in the industry, PCR samples need to be purified to allow efficient loading onto a capillary electrophoresis column. See Guttman, A., Cohen, A. S., Heiger, D. N. and Karger. B. L. (1990) Analytical and micropreparative ultrahigh resolution of oligonucleotide by polyacrylamide gel high-performance capillary electrophoresis, Anal. Chem. 62, 137–141, which is now incorporated herein by reference.

As has been discovered as part of the present invention, it has been shown that the offending substances are both the salt in the buffer and the deoxynucleotide triphosphates (dNTPs) which are present in the sample after PCR is completed. In accordance with the present invention, the offending substances are both the salt in the buffer and the deoxynucleotide triphosphates is in agreement with known considerations for sample loading which indicate that the amount of sample loaded on a column will be proportional to the resistivity of the sample and thus inversely proportional to the concentration of salt in the sample buffer.

In accordance with the present invention, provision is made to eliminate substantially all buffer salt and dNTPs from the sample and to leave the PCR product dissolved in pure H₂O for maximum loading efficiency. While other techniques can be used within the scope of the present invention, gel filtration High Performance Liquid Chromatography is the preferred separation means to eliminate substantially all buffer salt and dNTPs from the sample. As will be appreciated, however, chromatography in pure H₂O does not work well since the analytes themselves radically change the "buffer" composition locally, i.e., overloading is unavoidable. Moreover, most commercially available gel-filtration resins do not eliminate dNTPs when run in low salt, a problem which derives from the highly charged nature of the dNTPs and the partially charged nature of most chromatographic resins.

It is preferred that the gel filtration HPLC column 106 include a polymeric gel filtration medium, for example, poly(hydroxyethyl methacrylate), which provides adequate performance at low salt concentrations, for example 2 mM tris pH 8.0, 1 mM EDTA, to separate the dNTPs from primer and product. Such a polymeric gel filtration medium is available in the art and one which is preferred is one known in the art as HEMA-BIO 100 column available from Tessek Inc. It is within the scope of the present invention to utilize a HPLC column which is smaller, such as microbore or capillary LC columns, while still maintaining the desired separation but match more closely the volumes of the other components in the embodiment. Microbore chromatography techniques provide advantages of cost savings for solvents and an increase in signal due to the smaller elution volume.

It is to be understood that embodiments of the present invention can be arrived at which do not employ liquid chromatography. In such embodiments, suitable modifications are made to other components of the system.

Figure 2:
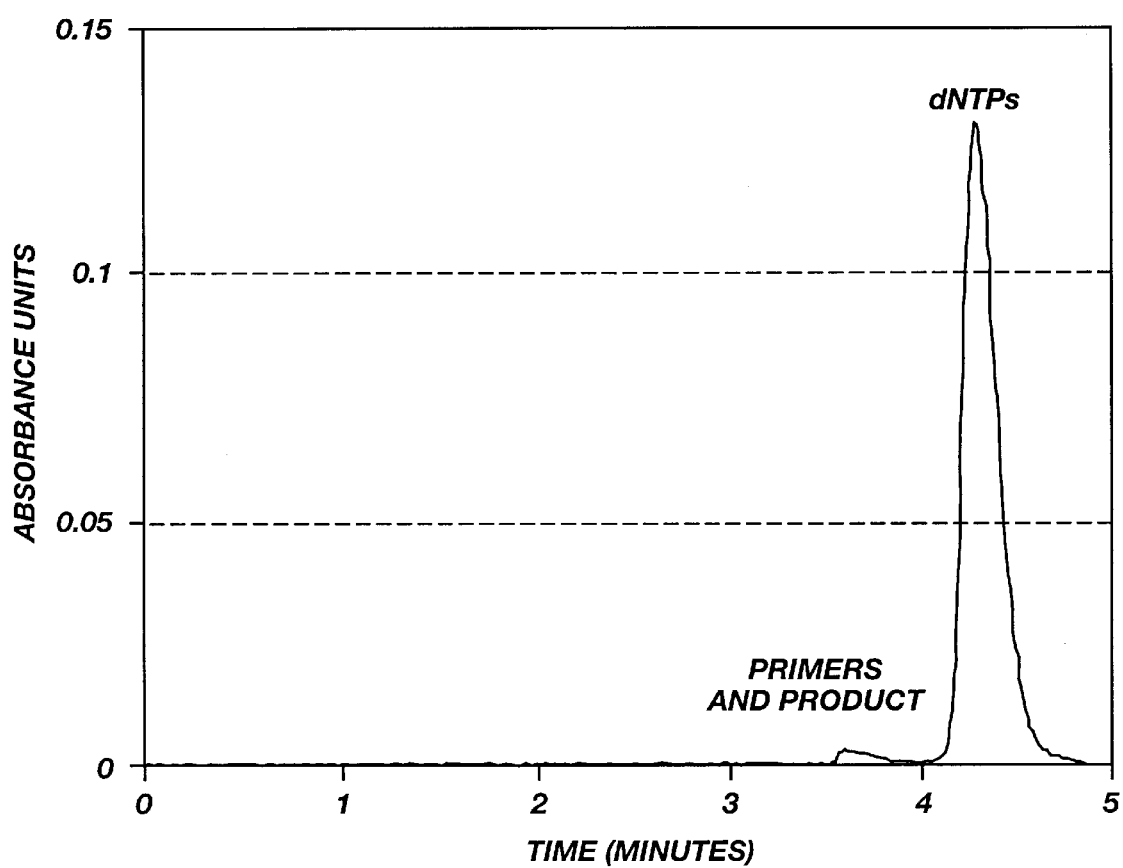
FIG. 2 is a chromatogram of exemplary results of the preferred gel filtration HPLC column described in connection with FIG. 1 using a low salt buffer.

FIG. 2 provides exemplary results of the preferred gel filtration HPLC column using a low salt buffer. FIG. 2 is a chromatogram of the PCR procedure performed with a 300 mer reaction product run isocratically in low salt buffer on the preferred gel filtration HPLC column 106. In FIG. 2, UV detection is at 260 nm. The first peak shown in FIG. 2 contains template DNA, primers and products. The second peak contains dNTPs. The salt and PCR buffer ingredients eluted at about ten minutes and are not represented in FIG. 2. Only the HPLC effluent obtained at three to four minutes are passed along for processing by the capillary electrophoresis column 116 at position 108A.

A heart cut valve 108 is provided to pass along the desired effluent (which in the described example is obtained at three to four minutes) to the tee 112 and the capillary electrophoresis column 116 at 108A. The reference "heart cut valve" is taken from the term of art in chromatography wherein the "heart cut" is defined as the central portion of a peak which is collected during processing of a sample. In this example, the reference "heart cut valve" is used to describe the function of an HPLC injection valve which allows the primer and product of the PCR procedure to be passed to the tee 112 and the capillary electrophoresis column 116 at position 108A. The effluent which exits the gel filtration HPLC column 106 before and after the primer and product of the PCR procedure, i.e., buffer dNTPs and salt, are directed to a waste chamber 109 at position 108B.

The heart cut valve 108 also functions to inject a high salt buffer chase 110 through the tee 112 at position 108B. The buffer chase 110 functions to reduce the undesirable effect which would occur if the negative end of the capillary electrophoresis column 116 stayed immersed in the low-salt buffer resulting in improper sample focusing and blurred peaks.

In accordance with the present invention, the tee 112 functions as a continuous sample loading device. The portion of the sample which is not loaded into the capillary electrophoresis column 116 flows through the tee 112 and continues to a second waste chamber 114. The second waste chamber 114 also functions as a negative buffer chamber for the electrophoresis procedure. A portion of the sample is loaded onto the capillary electrophoresis column 116 only if a voltage is present on the column 116, provided by a power supply 128 as available in the art, while the sample passes through the tee 112. The tee 112 advantageously allows sample loading into the capillary electrophoresis column 116 with no moving parts and without interrupting the flow of the sample or the electric field present in the capillary electrophoresis column 116.

The tee 112 can be fabricated by those skilled in the art using the information set forth herein. Advantageously, by varying the depth of insertion of the capillary electrophoresis column 116 into the tee 112 the efficiency of loading the capillary electrophoresis column 116 will be altered as will the bubble entrapment characteristics. It is presently preferred that the capillary electrophoresis column 116 be positioned in the tee 112 to block about one-third of the sample stream flowing through the tee. It will be appreciated that the tee 112 provides a significant advance over the art. In contrast to the prior art, the tee 112 advantageously allows continuous loading of the capillary electrophoresis column 116 without interruption of the sample stream flow and without interruption of the electric field applied to the capillary electrophoresis column 116. In the illustrated embodiment, the electric field must be present to obtain loading of the capillary electrophoresis column 116. As will be appreciated, the preferred embodiment utilizes continuous flow techniques to deliver the sample to the capillary electrophoresis column 116 and electrokinetic injection to load the capillary electrophoresis column 116. The latter avoids the problem of laminar flow in small diameter tubes (which produces a parabolic flow profile and disastrous band broadening, invalidating the electrophoresis results) which occurs when hydrodynamic loading techniques are used. The electrokinetic loading of the capillary electrophoresis column 116 provides significant advantages over the prior art.

One capillary electrophoresis column which is preferred for use with the present invention is fabricated from a tube available in the art having dimensions of 75 μm inner diameter, 375 μl outer diameter, and 75 cm length which is coated using Hjertén's method to eliminate electroosmotic flow. Hjertén, S. (1985) High-performance electrophoresis, Elimination of electroendosmosis and solute adsorption. *J. of Chromatogr.* 347, 191–198. For PCR analyses, the tube is filled with a 4% linear polyacrylamide solution (polymerized without bis-acrylamide) in 0.5 x TBE. Significantly, it is preferred to increase the catalyst (TEMED) and initiator (ammonium persulfate) many fold above conventional concentrations which decreases the average degree of polymerization (chain length). Increasing the catalyst and initiator concentrations many fold above conventional concentrations reduces viscosity of the polymer network and allows the solution to be replaced at a lower pressure. The lower viscosity tends to shorten analysis time at the expense of resolution. However, the described formulation still sieves DNA and allows efficient separation of PCR products from primer, primer-dimer, and from each other. The polymer gel may also be a cross-linked polyacrylamide gel. For DNA sequencing, it is preferred that a gel be used since gels have shown better resolution than their linear polymer counterparts.

It is also within the scope of the present invention to utilize replaceable polymers for DNA sequencing with the understanding that this would require higher pressure at the positive buffer chamber 120 with such higher pressure being easily accommodated. Moreover, viscosity of the polymer can be manipulated somewhat independently of sieving. It will also be appreciated that there is a tradeoff between speed of the procedure and the resolution of the procedure which is controlled by capillary electrophoresis column 116 length and the electric field present in the column 116. At relatively low electric fields (in the range from about 100 to about 300 V/cm), capillary sequencing gels can be used to interpret about 350 bases in under an hour. See Swerdlow, H., Dew-Jager, K. E., Brady, K., Grey, R., Dovichi, N. J. and Gesteland, R. (1992) Stability of capillary gels for automated sequencing of DNA, Electrophoresis 13, 475–483, which is now incorporated herein by reference. High speed, relatively low-resolution DNA separations are possible in polymer solutions at high electric fields (in the range from about 500 to about 1000 V/cm), conditions which would normally rapidly break down cross-linked gels. Such analyses are useful for repetitive sequencing of short regions of DNA.

A temperature control system 144, which can be fabricated by those skilled in the art using the information set forth herein, is preferably included to maintain the temperature of the gel filtration HPLC column 106 and the capillary electrophoresis column 116. The temperature control system 144 should provide greater reproducibility accurate control since viscosity and electrophoretic mobility vary 2% per degree centigrade change in temperature.

The structure used for detection of the DNA species will now be described. The DNA species migrate down the described capillary electrophoresis column 116 about 25 cm and are visualized by an on-column laser-induced fluorescence detector 118. It is preferred that the laser-induced florescence detector 118 utilize a green Helium-Neon laser 132 operating at 543 nm which is focused onto the capillary electrophoresis column 116 to excite the fluorescent dye, described above, which labels at least one of the PCR primers.

The light emitted by the sample is collected by a microscope objective 134 and is subjected to both a spatial filter device 136 and a spectral filter device 138 to eliminate scatter. Detection is preferably achieved with a photomultiplier tube 140 and a processor 142 wherein a current signal provided by the photomultiplier tube and its power supply 140 is converted to a voltage, subjected to analog filtering, digitized and then preferably dispatched to a general purpose computing device 130. It is preferred that the general purpose computing device 130 be a PC compatible computer.

The general purpose computing device 130 preferably includes programming code and interface devices which can readily be provided by those skilled in the art using the information set forth herein, to coordinate and control the operation of the HPLC pump 100, the thermal cycling device 104, the HPLC injection valve 105, the heart cut valve 108, the laser-induced fluorescence detector 118, and the power supply 128. The valves 105 and 108 represented in FIG. 1 are preferably controlled by digitally controlled actuators and computing device 130. The power supply 128 for the capillary electrophoresis column 116, the photomultiplier tube and its power supply 140, the laser 132, the HPLC pump 100, and the thermal cycling device 104 are all switched on and off as necessary by the computing device 130. The pressure to the buffer chase chamber 110 and the refill buffer chamber 124 are each switched by a solenoid valve (113 and 122, respectively) between atmospheric pressure and a 100 psi pressure supply (111 and 124, respectively) with the solenoid valves being controlled by the computing device 130. Automation of the embodiment provides precise control over all timing aspects of the cycling, purification and separation, and thus a very high degree of reproducibility.

Still referring to FIG. 1, before the fluorescent species reaches the end of the capillary electrophoresis column 116, the run ends and the capillary is refilled from clean polymer buffer taken from the positive buffer chamber 120. Filling is accomplished by application of pressure from the pressure source 124 to the positive buffer chamber 120 via a pneumatic valve system 122. After the run, the capillary electrophoresis column 116 represented in FIG. 1 is ready for processing of a new sample.

As used herein, sterilization refers to the elimination or inactivation of substantially all undesired material, in particular materials such as template DNA and amplified products from the previous PCR procedure. Sterilization is accomplished by a loop wash device 126, which preferably includes a supply of HCl or NaOH, which can be heated to a suitable temperature by the thermal cycler which is preferably automatically controlled by the computing device 130.

From the foregoing, it will be appreciated that the present invention provides on-line DNA analysis. As used herein, the term "on-line" refers to the apparatus and accompanying methods which subject a sample to thermal cycling and then transfer the sample without the intervention of any technician to another apparatus for further analysis or identification. In this case, the flow from an HPLC pump 100 delivers a flow of liquid to the injection valve 105 which carries said sample to a primary separation means such as the gel filtration HPLC column 106 to remove unwanted salts and reactants from the DNA product. In the preferred embodiment, the DNA product eluting from the gel filtration HPLC column 106 is then injected into the capillary electrophoresis column 116 advantageously using the tee 112 and through the application of sufficient voltage to cause an electrokinetic loading of the sample into the column. In the preferred embodiment of FIG. 1, capillary electrophoresis column 116 functions as a secondary separation means. Detection of the DNA sample is performed with any of a number of different detection means, and preferably the laser-induced fluorescence detector 118 located on the capillary electrophoresis column 116, as the sample migrates past a given point on said column.

For DNA sequencing in the described capillary fluidic apparatus, the elimination of template DNA is of paramount importance. Template DNA remaining in a sequencing sample forms a narrow region of low conductivity, which causes localized heating and gel instability, especially when using strong electric fields. Uracil-containing template DNA was eliminated by the use of uracil DNA glycosylase, high pH and high temperature all of which are fully compatible with the described apparatus. Solid phase methods based on magnetic beads coated with streptavidin and biotin-containing templates may also be used. Alternatively, a primary or secondary chromatographic separation system could be used to eliminate template DNA. Large template molecules such as m13 could be eliminated by gel-filtration on the basis of their size compared to sequenced fragments. PCR-produced templates could be targeted for removal by the use of a suitable 5' end group on one of the primers. Alternatively, the fluorescent moiety of the sequenced fragments could be used for an affinity or reversed phase separation.

Again for DNA sequencing, a four-channel rotating filter wheel can replace the filter 136 and is preferably included for use when multiple wavelength detection arrangements are used. See Swerdlow, H., Zhang, J. Z., Chen, D. Y., Harke, H. R., Grey, R., Wu, S., Dovichi, N. J. and Fuller, C. (1991) Three DNA sequencing methods using capillary gel electrophoresis and laser-induced fluorescence, *Anal. Chem.* 63, 2835–2841, which is now incorporated herein by reference.

Figure 3:
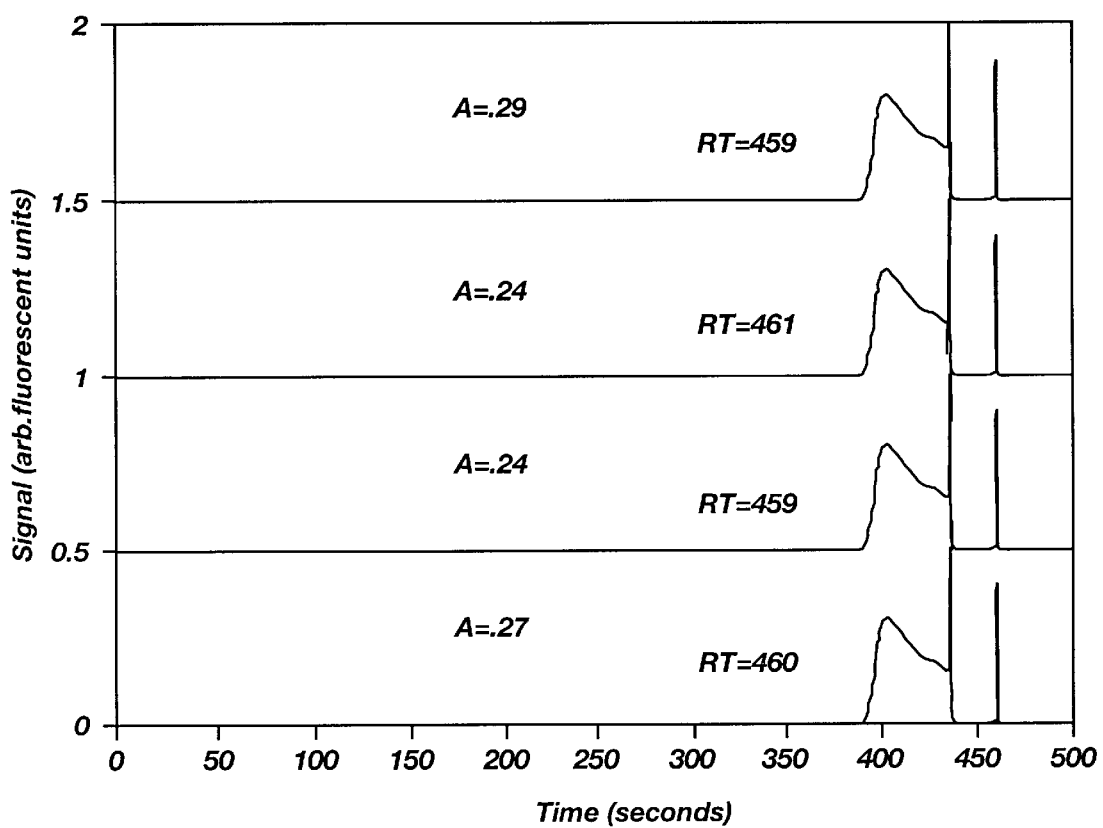
FIG. 3 is a diagram showing the results of four consecutive runs including PCR and electrophoresis procedures using the embodiment represented in FIG. 1.

Reference will next be made to FIG. 3 which is a diagram showing the results of four consecutive runs including PCR and electrophoresis procedures using the embodiment represented in FIG. 1. Each consecutive run was completed in no more than about 20 minutes, although using the embodiment represented in FIG. 1, each run can be completed in much less time, preferably about 14 minutes. In the four consecutive runs which are represented in FIG. 3 the thermal cycling procedure was accomplished in about eight minutes, the purification procedure (HPLC) was accomplished in about four minutes, and the electrophoresis procedure was accomplished in about eight minutes.

As can be seen from FIG. 3, baseline noise for each run is very low. FIG. 3 desirably does not exhibit any sharp noise peaks, also referred to as "spikes," which would be due to particulates in the sample but are eliminated by the HPLC procedure. Moreover, FIG. 3 also desirably exhibits no spikes due to bubbles created during the loading of the capillary electrophoresis column 116. The direct loading of the capillary electrophoresis column 116 using the tee 112 and the technique described above provides the desirable results. Those skilled in the art will appreciate that particulates and bubbles in the sample have been common problems and are frequently seen in prior capillary electrophoresis techniques. The present invention provides an effective solution to these problems.

As can been seen in FIG. 3, the signal is more than ample for product identification using the embodiment of FIG. 1. The signal-noise ratio is about 490:1 for the 303 bp peak in the first run (represented on the bottom of FIG. 3). Moreover, as represented in FIG. 3, the peak heights and areas are near constant. Employing the loop wash device 126 between runs enhances reproducibility. It will be appreciated that the resulting signal strength is affected by the concentration of the low salt buffer, the strength of the electric field employed while loading, and the flow rate of the chromatographic separation.

Most desirably, FIG. 3 shows that the retention times and peak widths of a primer and product are virtually identical for the four runs depicted in FIG. 3. FIG. 3 shows that the retention times for the four runs vary only ±1 second for the four runs. Overall retention time reproducibility is excellent and average coefficients of variation (100 times the standard deviation divided by the mean) for the product peak were 0.9% (n=15) each day, 0.9% (n=21) for each capillary electrophoresis column, and 1.6% (n=21) between two capillary electrophoresis columns. The error in retention times includes both the chromatographic and capillary electrophoretic contributions. As will be appreciated by those skilled in the art, the noted variation is small and other embodiments of the present invention can be fabricated to provide even better results.

Figure 4A:
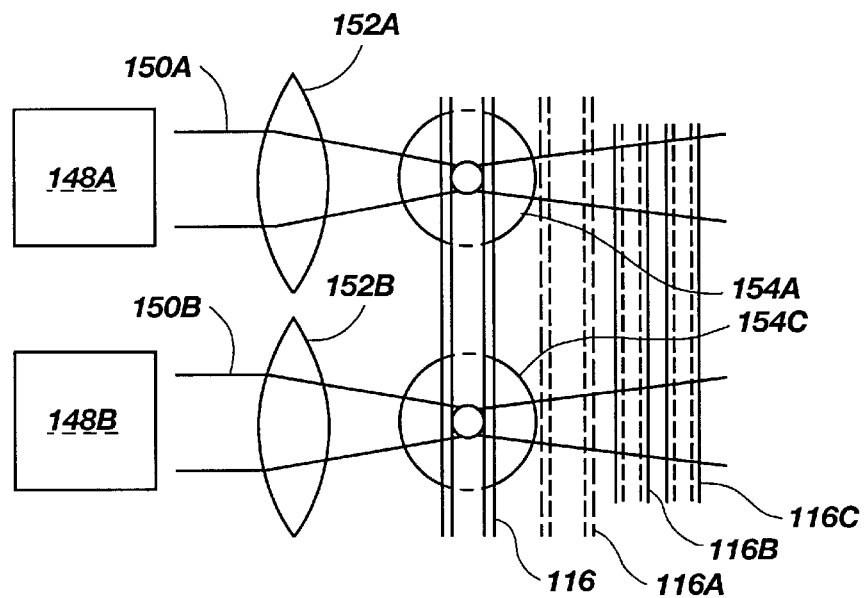
FIGS. 4A–B are side and top schematic views, respectively, of a florescence detector within the scope of the present invention.
Figure 4B:
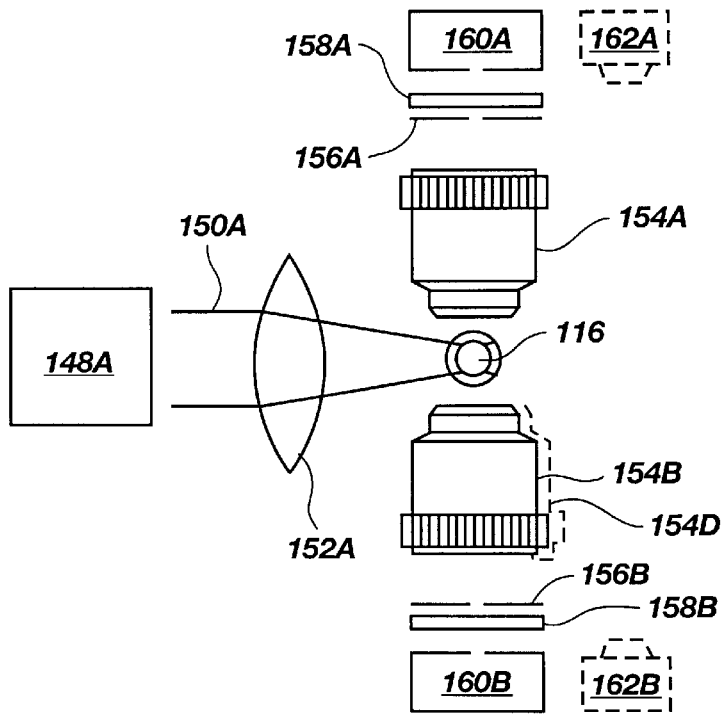

An alternative four color fluorescence detector which contains no moving parts is represented in the FIGS. 4A & 4B, which are side and top schematic views, respectively. Represented in the figures are two lasers beams 150A & 150B produced by laser devices 148A & 148B, respectively.

The laser beam 150A has, for example, an argon 488 nm line to excite dyes known in the industry as FAM (540 nm) and JOE (560 nm) and available from Applied Biosystems. The laser beam 150B has, for example, a green helium-neon 543 nm line to excite dyes known in the industry as TAMRA (580 nm) and ROX (610 nm) and available from Applied Biosystems. It will be appreciated that as new dyes and lasers emitting suitable wavelengths become available, such dyes and lasers can be utilized in accordance with the present invention. The described fluorescence detector provides a modular approach to detection and provides great advantages over the prior art.

The laser beams 150A & 150B are focused by lenses 152A & 152B, respectively, to spots within the interior of the capillary electrophoresis column 116. The focused laser beam spots are separated by a few centimeters on the capillary electrophoresis column to prevent cross-talk between the channels from scattered light. The temporal offset between the separated laser signals can be easily corrected since the velocity of analytes through the capillary electrophoresis columns is precisely known.

As illustrated in the top view of FIG. 4B, fluorescence is simultaneously collected from two sides of the capillary electrophoresis column 116 at each laser beam focus. With four independent collection optics, the structures represented in FIGS. 4A & 4B suffer neither from duty cycle nor beam-splitter losses that are common in the previously available devices. Advantageously, the structure of FIGS. 4A & 4B is simple, robust, sensitive and has no moving parts.

It is preferred that two optical assemblies, which preferably comprise microscope objectives, are provided on each side of the capillary electrophoresis column 116. Two optical assembles 154B and 154D are positioned one side of the capillary electrophoresis column 116. The two remaining optical assemblies 154A & 154C are positioned on the other side of the capillary electrophoresis column 116. The two uppermost optical assemblies being indicated at 154A & 154B in FIG. 4B. The optical assemblies are preferably oriented substantially perpendicularly to the direction of propagation of the laser beams 150A & 150B. In addition to the optical assemblies, the collected fluorescence is preferably passed through an aperture plate 156A & 156B (preferably a pinhole aperture), and a filter 158A & 158B before being received by a photomultiplier tube 160A & 160B. Alternatively, a charge coupled device (CCD) (two of which are represented at 162A & 162B) can be used as a detection device. The signals produced by the detection devices are conveyed to appropriate signal processing and computing structured as described earlier, including computing device 130, and as can be devised by those skilled in the art using the information set forth herein.

As will be explained shortly, the fluorescence detector can be used with more than one capillary electrophoresis column with additional exemplary capillary electrophoresis columns being indicated at 116A–C.

The CCD devices 162A–B are preferred to detect the fluorescent light in all the capillary electrophoresis columns simultaneously. When using CCD devices, hardware and software is available in the industry to sum the CCD pixels corresponding to each column while separating the signals from adjacent columns in real time. Those skilled in the art can use the information set forth herein to create the programming code which is necessary to transform the information from the detection device into a genotype, a clinical diagnosis or a DNA sequence using the computing device 130.

It is also within the scope of the present invention to utilize rectangular capillary columns in a sandwich configuration to allow one laser beam to simultaneous excite a plurality of columns as described in connection with FIGS. 4A–B. Such rectangular columns preferably have dimensions of 50 $\mu$m×500 $\mu$m (inner dimensions). Embodiments of the present invention may include a single capillary electrophoresis column, three capillary electrophoresis columns, ten capillary electrophoresis columns, ninety-six capillary electrophoresis columns, or any other number necessary for the desired application.

Other detection structures can also be used within the scope of the present invention. For example, a confocal scanner, a multi-capillary sheath-flow cuvette, and a structure using fiber-optic excitation of individual capillaries and a charge-coupled-device (CCD) camera, can all be used within the scope of the present invention. Information on these other detection structures can be found in the following publications which are all now, or have already been, incorporated herein by reference: Huang, X. C., Quesada, M. A. and Mathies, R. A. (1992) DNA sequencing using capillary array electrophoresis, *Anal. Chem.* 64, 2149–2154; Kambara, H. and Takahashi, S. (1993) Multiple-sheathflow capillary array DNA analyzer, *Nature* 361, 565–566; Taylor, J. A. and Yeung, E. A. (1993) Multiplexed fluorescence detector for capillary electrophoresis using axial optical fiber illumination, *Anal. Chem.* 65, 956–960; and, Karger, A. E., Harris, J. M. and Gesteland, R. F. (1991) Multi-wavelength fluorescence detection for DNA sequencing using capillary electrophoresis, *Nucleic Acids Res.* 19, 4955–4962.

Moreover, infrared dyes for labelling DNA can also be used within the scope of the present invention. Use of infrared dyes and infrared emitters offer advantages in both sensitivity and instrument design for fluorescent detection. When using infrared dyes and corresponding detection structures, the signal to noise ratio is improved because background fluorescent emissions are far lower in the infrared portion of the electromagnetic spectrum. Alternatively, time-resolved fluorescent detection in the infrared portion of the spectrum can provide an accurate way to distinguish fluors. Even further, by simultaneous use of both visible and infrared portions of the spectrum, simultaneous detection of two sequencing reactions in a single capillary is also possible.

It is also within the scope of the present invention to use a sheath-flow cuvette, represented schematically at 149 in FIG. 1, as part of the fluorescence detector if poor signal-to-noise ratios are a problem. Use of a sheath-flow cuvette provides at least an order of magnitude better limit of detection as described in Swerdlow, H. et al., Three DNA sequencing methods using capillary gel electrophoresis and laser-induced fluorescence, which has already been incorporated herein by reference. Those skilled in the art will be able to make the necessary adaptations to the flow stream due to the cuvette's location at the far end of the capillary electrophoresis column 116 where the pressure source 124, the pneumatic valve system 122, and positive buffer chamber 120 are situated in FIG. 1. If a sheath-flow cuvette 149 is used, refilling of the capillary electrophoresis column 116 is possible directly through the sheath flow cuvette in which case the polarity of the power supply is switched to allow the cuvette to be grounded. Alternatively, a three-port valve, schematically represented at 147 in FIG. 1, can be installed between the tee 112 and the negative second waste chamber 114 (also referred to as the negative buffer chamber) allowing a pump, schematically represented at 145, to refill the capillary from the tee 112 end.

Figure 5:
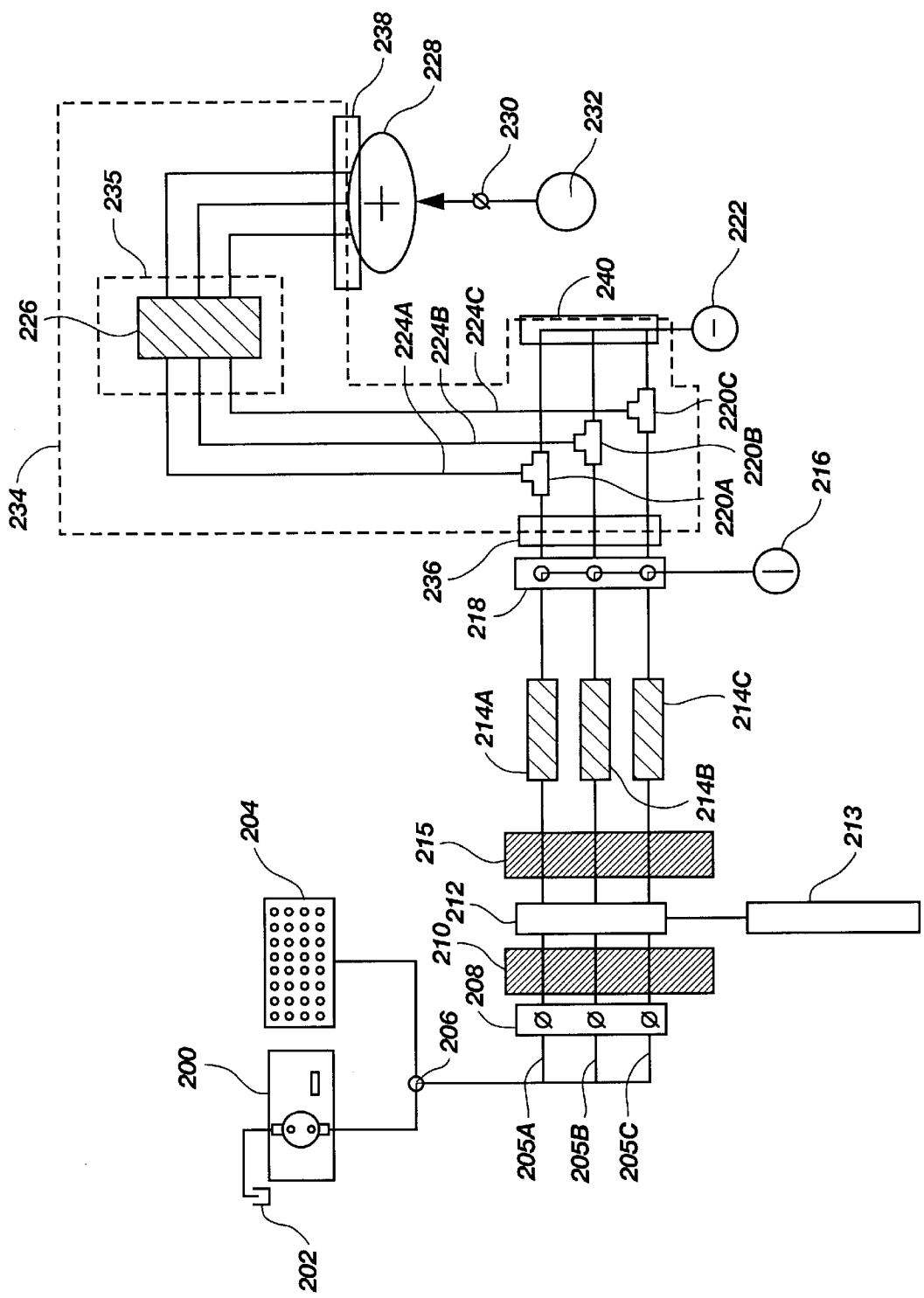
FIG. 5 is a schematic diagram of a second presently preferred embodiment of the present invention.

Another embodiment of the present invention will next be described by reference to FIG. 5. FIG. 5 is a schematic diagram of a second presently preferred embodiment of the present invention. The embodiment represented in FIG. 5 provides greatly increased throughput of the PCR reaction analysis or DNA sequencing system which incorporates a plurality of parallel sample flowstreams. It will be appreciated that the increased throughput of the embodiment represented in FIG. 5 provides great benefits.

While the embodiment represented in FIG. 5 illustrates three parallel fluid channels, represented at 205A–C, many more parallel fluid channels, for example fifty, are possible within the scope of the present invention. It is to be understood that many of the components and methods described above are also applicable to the embodiment of FIG. 5 even though not explicitly indicated to avoid unnecessary repetition. The embodiment of FIG. 5 is preferably fed by an autosampler 204, as known in the art, and a HPLC pump 200 with a low salt buffer reservoir 202 (similar to that discussed above at 102) which are interconnected and connected to downstream devices by a three way valve 206.

A first valve manifold 208 is provided to fill a given channel, with the valve for that channel being opened, while the valves for the other channels are closed. A first thermal cycling device 210 is provided which can simultaneously hold and homogeneously heat and cool all of the channels 205A–C. After the thermal cycling device 210, each channel passes through a second manifold 212. The second manifold 212 functions to add sequencing agents from at least one mixing chamber and at least one pump, both represented at 213, when DNA sequencing is to be carried out. Also when DNA sequencing is to be carried out a second thermal cycling device 215 subjects each of the channels 205A–C to thermal cycling. The HPLC pump 200 will run all of the samples in channels 205A–C through the first and second manifolds 208 & 212 and through the first and second thermal cycling devices 210 & 215 and to the HPLC columns 214A–C.

A three-way valve manifold 218 is provided to connect a high-salt buffer chase pump 216 to the channels 205A–C. Multiple tees 220A–C are provided, each tee 220A–C loading an individual capillary electrophoresis column 224A–C. Each capillary electrophoresis column 224A–C is grounded via a common waste and negative buffer chamber 222 and each capillary electrophoresis column 224A–C is refilled from a common positive buffer chamber 228 accompanied by a pressure source 232 and pneumatic valve 230.

The fluorescence detector represented at 226 is preferably a multiple column fluorescence detector such as the detector represented in FIGS. 4A–B multiplied by the number of columns. Importantly, structures are provided to change the capillary electrophoresis columns 224A–C while keeping the optics described in connection with FIGS. 4A–B properly aligned. Alignment of the detection structures is preferably accomplished with a jig 235 having locator pins or an equivalent structure to maintain exact alignment of the laser beams and the other structures in the optical path. It is within the scope of the present invention that the tees 220A–C, capillary electrophoresis columns 224A–C, and the fluorescence detector jig 235, are all included as a disposable unit 234. An adjustment structure can be provided to adjust the alignment of the tees 220A–C with the capillary electrophoresis columns 224A–C or the adjustment of the tees 220A–C can be pre-set. At the positive end of the capillary electrophoresis columns 224A–C a mating structure 238 is provided to simultaneously connect all of the capillary electrophoresis columns 224A–C to the positive buffer chamber 228. At the negative end of the capillary electrophoresis columns 224A–C a mating structure 240 is provided to simultaneously connect all of the capillary electrophoresis columns 224A–C to the negative buffer chamber 222. Another mating structure 236 is provided to simultaneously connect all of the tees 220A–C to the three-way manifold 218.

Importantly, when the embodiments of the present invention are used to perform DNA sequencing the differences between dye-primers and dye-terminators must be considered. Dye-terminators, or peak-height encoding, is preferred for use with the present invention since it allows a single reaction per template. Advantageously, in the fluidic system of the present invention, dye-terminators require only one reaction channel per template. If a dye system is used which requires four separate reactions, four separate flow channels will be provided, so that four different reactions will be performed and the samples will be combined before high performance liquid chromatography.

It will be appreciated that the present invention has many applications other than those already described and outside the direct scope of genome sequencing. For example, the present invention's ability to efficiently perform PCR and/or sequencing and direct capillary electrophoresis separations would be useful in mutational analysis, genotyping and diagnostics. When used for mutational analysis of large populations, embodiments of the present invention include devices to carry out blood preparation as a front end task. One of the numerous protocols which have been reported for preparation of DNA from whole blood for PCR can be adapted for use with the present invention. One preferred protocol best suited for use with the present invention is formamid low temperature PCR (FoLT-PCR) which is described in Panaccio, M., Gergesz, M. and Lew, A. M. (1993) FoLT PCR: A simple PCR protocol for amplifying DNA directly from whole blood, *BioTechniques* 14, 238–243 which is now incorporated herein by reference. The use of formamid in the extraction buffer allows whole blood to be used directly in a PCR reaction. An embodiment of the present invention for performing genomic sequencing would preferably have two thermal control portions, one for PCR and one for DNA sequencing as can be arrived at using the information provided above.

Genotyping is another application which benefits greatly from the present invention. The present invention provides a large increase in throughput compared with the available art. For minisatellite analyses, fragments are a few kilo-base pairs in length; low concentration polymer-filled (e.g. hydroxyethyl cellulose) capillary electrophoresis columns should be sufficient. For microsatellites, lengths are typically less than 300 bp and resolution of a few necleotides is required. An embodiment of the present invention using polymer filled capillary electrophoresis can readily provide the resolution necessary for such genotyping tasks.

The present invention can also be beneficially used in DNA-based diagnostics. Some DNA-based diagnostics only require knowledge of the presence or absence of a specific PCR product to be informative. This class of diagnostics includes bacterial and viral identification, e.g., Tuberculosis testing. The embodiments of the present invention can easily and quickly provide such results. As indicated above, it is within the scope of the present invention to provide a blood preparation subsystem on the front end of the described embodiments which would make point-of-care diagnosis widely available using the present invention.

Another class of DNA-based diagnostics requires the ability to sequence DNA directly from real samples and generally includes PCR as a first step. This class of DNA-based diagnostics includes subtype and serotype identification for viruses and bacteria, analysis of oncogene hot-spots for early cancer diagnosis, and forensic analysis of trace hair and blood samples.

The present invention provides a complete automated DNA analysis and sequencing system. Primer-walking techniques can be used with standard or cycle sequencing within the scope of the present invention. Alternatively, mapping of transposon-insertions allows directed sequencing of cosmids; PCR reactions proceed directly from colonies or overnight cultures and the products are then sequenced. After purification, sequencing reactions are loaded automatically and run on a polymer-filled capillary electrophoresis column or capillary gel electrophoresis column and analyzed with a four channel laser-induced fluorescence detector. With the present invention, the entire process takes no more than about 1.5 hrs per template.

In contrast to the slow performance of the previously available devices, an embodiment of the present invention including 100 capillary electrophoresis column produces 625 nucleotides per capillary electrophoresis column per each 1.5 hours which results in one million nucleotides/day. Using a directed sequencing strategy, three or four embodiments of the present invention could finish a megabase of DNA sequence in a single day if the large-scale mapping and subcloning challenges are suitably met.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. An apparatus for subjecting a biological sample to rapid thermal cycling and subsequent on-line analysis of DNA products derived therefrom, the apparatus comprising:

means for holding a liquid biological sample;

first means for controlling and rapidly varying a temperature of the means for holding a liquid biological sample at a rate at least as great as one degree centigrade per second repeatedly through a predetermined temperature cycle such that the temperature repeatedly ramps from a first temperature to at least a second higher temperature and ramps from at least the second temperature to a lower temperature where said predetermined temperature cycle facilitates DNA amplification;

a primary separation means for separating one or more components of the liquid biological sample, the primary separation means being spaced from the first means for controlling and rapidly varying a temperature of the means for holding a sample;

means for fluidic transferring of the liquid biological sample from the means for holding the liquid biological sample to the primary separation means;

a secondary separation means for separating the components of the liquid biological sample;

means for fluidic transferring of at least some of the liquid biological sample from the primary separation means and injecting at least some of the liquid biological sample components into the secondary separation means;

means for detecting one or more separated components of interest in the secondary separation means; and means for controlling the first means for controlling and rapidly varying the temperature of the liquid biological sample such that thermal cycling of the biological sample and the desired DNA amplification is carried out, and for controlling the primary separation means such that primary separation is carried out, and for controlling the secondary separation means such that secondary separation is carried out, and for controlling the means for detection such that detection is carried out on the liquid biological sample and the liquid biological sample is analyzed without manual intervention.

2. The apparatus in claim 1 wherein said primary separation means is a liquid chromatograph apparatus.

3. The apparatus in claim 1 wherein said secondary separation means is an electromigration apparatus.

4. The apparatus in claim 1 wherein said sample holding means is a liquid chromatography injection valve.

5. The apparatus in claim 1 wherein the primary separation means is an electromigration apparatus.

6. The apparatus in claim 1, further comprising second means for controlling and rapidly varying the temperature of the means for holding a sample repeatedly through a predetermined temperature cycle.

7. An apparatus for subjecting a liquid biological sample to rapid thermal cycling and subsequent on-line analysis of DNA products derived therefrom, the apparatus comprising:

means for holding a liquid biological sample;

first means for controlling and rapidly varying a temperature of said liquid biological sample at a rate at least as great as one degree centigrade per second repeatedly through a predetermined temperature cycle such that the temperature repeatedly ramps from a first temperature to at least a second temperature and ramps from the second temperature to a lower temperature and where said predetermined temperature cycle facilitates DNA amplification of said liquid biological sample;

a primary separation means for separating one or more components of the liquid biological sample, the primary separation means being spaced from the first means for controlling and rapidly varying a temperature of the liquid biological sample;

means for fluidic transferring of said liquid biological sample from the means for holding said liquid biological sample to the primary separation means;

a secondary separation means for separating the components of the liquid biological sample;

means for fluidic transferring of at least some of the liquid biological sample from the primary separation means and injecting at least some of the liquid biological sample components into the secondary separation means, the fluidic transfer to the secondary separation means being continuous;

temperature control means for maintaining the temperature of the primary separation means and the secondary separation means;

means for removing salt from the liquid biological sample;

means for detecting one or more separated components of interest in the secondary separation means; and means for controlling the first means for controlling and rapidly varying the temperature of the liquid biological sample such that thermal cycling of the biological sample and DNA amplification is carried out, and for controlling the primary separation means such that primary separation of DNA derivatives is carried out, and for controlling the secondary separation means such that secondary separation of DNA derivatives is carried out, and for controlling the means for detection such that detection of DNA derivatives is carried out on the sample and the sample is analyzed without manual intervention.

8. The apparatus in claim 7 wherein said primary separation means is a liquid chromatograph apparatus.

9. The apparatus in claim 7 wherein said secondary separation means is an electromigration apparatus.

10. The apparatus in claim 7 wherein said sample holding means is a liquid chromatography injection valve.

11. The apparatus in claim 7 wherein the primary separation means is an electromigration apparatus.

12. The apparatus in claim 7 wherein the secondary separation means comprises means for collecting fractions from the biological sample.

13. The apparatus in claim 7, further comprising second means for controlling and rapidly varying the temperature of the liquid biological sample repeatedly through a predetermined temperature cycle.

* * * * *